(12) United States Patent
Tateyama

(10) Patent No.: US 8,343,765 B2
(45) Date of Patent: Jan. 1, 2013

(54) GENE INJECTION APPARATUS AND GENE INJECTION METHOD

(75) Inventor: Kiyohiko Tateyama, Sagamihara (JP)

(73) Assignee: Olympus Corporation, Tokyo (JP)

( * ) Notice: Subject to any disclaimer, the term of this patent is extended or adjusted under 35 U.S.C. 154(b) by 180 days.

(21) Appl. No.: 12/475,023

(22) Filed: May 29, 2009

(65) Prior Publication Data

US 2009/0291502 A1    Nov. 26, 2009

Related U.S. Application Data

(63) Continuation of application No. PCT/JP2007/069798, filed on Oct. 11, 2007.

(30) Foreign Application Priority Data

Nov. 30, 2006 (JP) ................. 2006-324933

(51) Int. Cl.
*C12N 15/87* (2006.01)
*C12M 1/00* (2006.01)

(52) U.S. Cl. .................... 435/455; 435/285.1

(58) Field of Classification Search .......... None
See application file for complete search history.

(56) References Cited

U.S. PATENT DOCUMENTS

| | | |
|---|---|---|
| 2003/0228695 A1 | 12/2003 | Nakamura et al. |
| 2007/0087436 A1 | 4/2007 | Miyawaki |

FOREIGN PATENT DOCUMENTS

| | | |
|---|---|---|
| JP | 11-347971 A | 12/1999 |
| JP | 2003-325161 | 11/2003 |
| JP | 2005-52134 | 3/2005 |
| WO | WO 2004/092369 A1 | 10/2004 |

OTHER PUBLICATIONS

Yamamoto et al (Experimental Cell Research. 1982; 142: 79-84).*
Furusawa et al (In vivo and in vitro erythropoiesis: the Friend system. 1980. Editor: GB Rossi).*
Miller et al. (BioTechniques. Aug. 2002; 33: 366-375).*
Yamamoto F. et al., "The 'Pricking 'Method A New Efficient Technique for Mechanically Introducing Foreign DNA into the Nuclei of Culture Cells", Experimental Cell Research (1982), vol. 142, pp. 79-84.
Kudo, Akira et al., "Structure of thymidine kinase gene introduced into mouse Ltk- cells by a new injection method", Gene (1982), vol. 19, pp. 11-19.
Yamamoto, Fumichiro et al., "Intracellular Introduction of a Fixed Quantity of Substances by Pricking Cells Using a Modified Microscope", Experimental Cell Research (1981), vol. 135, pp. 341345.
Japanese Office Action dated Jun. 5, 2012 in related Japanese Patent Application No. 2006-324933.

* cited by examiner

*Primary Examiner* — Scott Long
(74) *Attorney, Agent, or Firm* — Scully, Scott, Murphy & Presser, P.C.

(57) ABSTRACT

A gene injection apparatus for injecting a gene into a cell held on a substrate, includes a needle unit. The needle unit includes a fine needle to be inserted into the cell immersed in a culture medium in which the gene is dispersed, and a flexible support part configured to hold the fine needle, the flexible support part being flexing when the fine needle is pressed onto the substrate. The gene injection apparatus further includes a drive unit configured to push down the flexible support part toward the substrate, further from a position where a tip of the fine needle contacts the substrate.

8 Claims, 10 Drawing Sheets

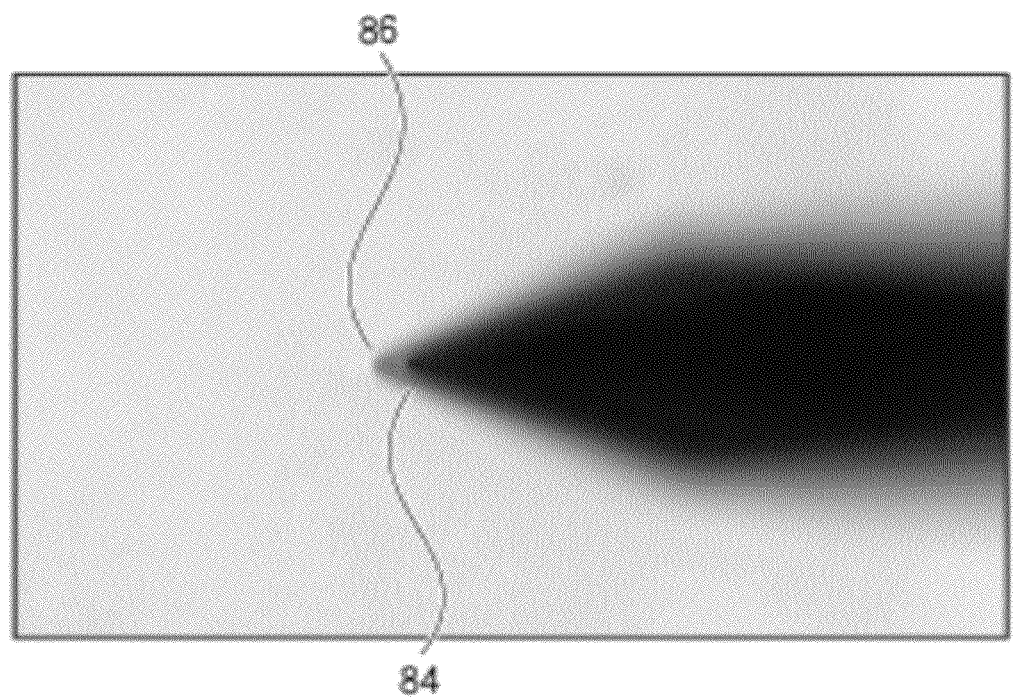
F I G. 8

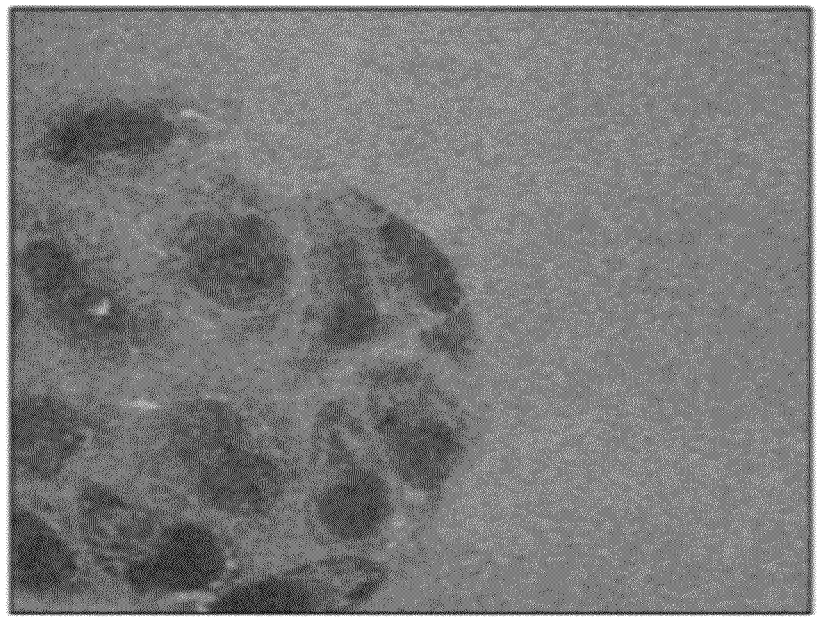
F I G. 9A
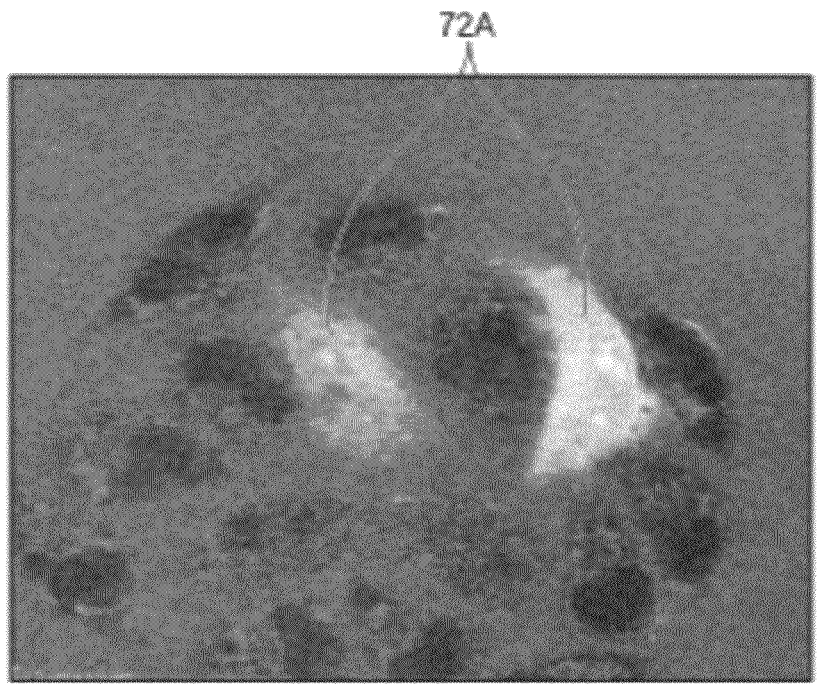
F I G. 9B

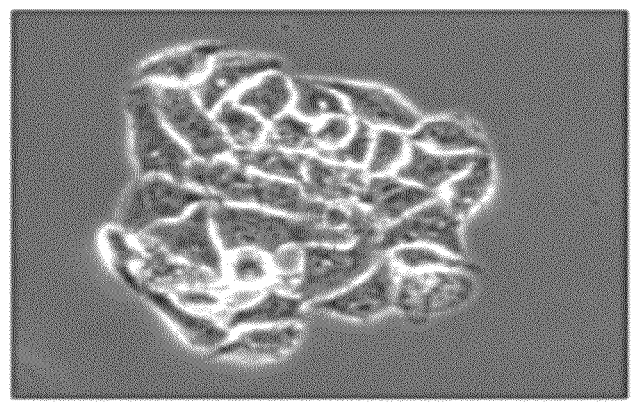
F I G. 10A
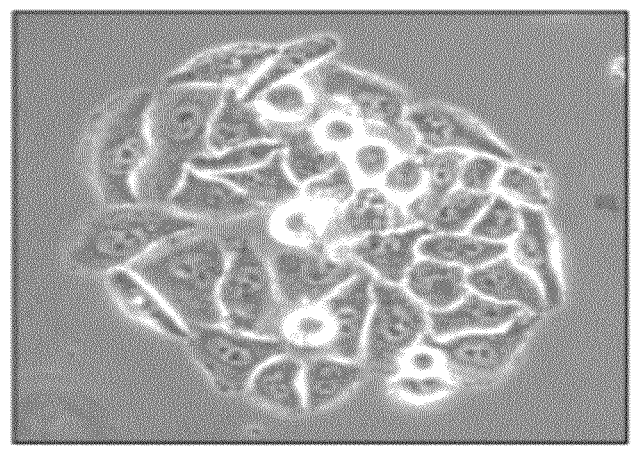
F I G. 10B
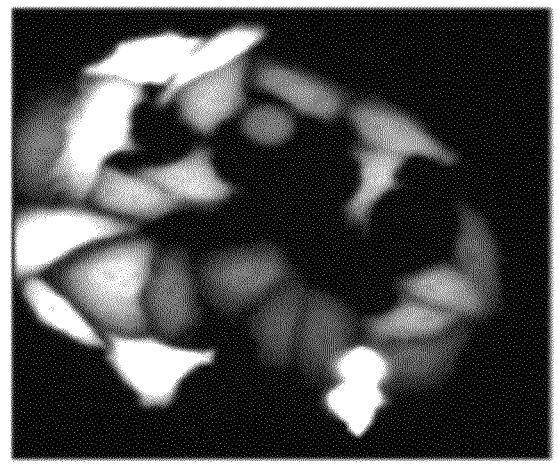
F I G. 10C

GENE INJECTION APPARATUS AND GENE INJECTION METHOD

CROSS REFERENCE TO RELATED APPLICATIONS

This is a Continuation Application of PCT Application No. PCT/JP2007/069798, filed Oct. 11, 2007, which was published under PCT Article 21(2) in Japanese.

This application is based upon and claims the benefit of priority from prior Japanese Patent Application No. 2006-324933, filed Nov. 30, 2006, the entire contents of which are incorporated herein by reference.

BACKGROUND OF THE INVENTION

1. Field of the Invention

The present invention relates to a gene injection apparatus and a gene injection method.

2. Description of the Related Art

Publication WO04/092369 (US 2007/0087436 A1) discloses a microinjection method and a microinjection apparatus, both designed to electrically adsorb substance, such as a gene, to the tip of a fine needle, project the fine needle into a cell and apply a pulse voltage to the fine needle, thereby to inject the substance into the cell. The fine needle is projected into the cell, by using a piezoelectric element that can elongate and contract in the axial direction of the fine needle.

The system disclosed in the above-identified publication is of the type in which the fine needle holds a gene at its tip. Hence, the gene can be injected into the cell with low-invasive to the cell, increasing the survival rate of the cell.

BRIEF SUMMARY OF THE INVENTION

According to a first aspect of the present invention, there is provided a gene injection apparatus for injecting a gene into a cell held on a substrate, comprising:

a needle unit having a fine needle to be inserted into the cell immersed in a culture medium in which the gene is dispersed, and a flexible support part configured to hold the fine needle, the flexible support part being flexing when the fine needle is pressed onto the substrate; and a drive unit configured to push down the flexible support part toward the substrate, further from a position where a tip of the fine needle contacts the substrate.

According to a second aspect of the present invention, there is provided a gene injection method for injecting a gene into a cell held on a substrate, by using a needle unit having a fine needle to be inserted into the cell immersed in a culture medium in which the gene is dispersed, and a flexible support part configured to hold the fine needle, the flexible support part being flexing when the fine needle is pressed onto the substrate, the method comprising:

inserting the fine needle into the cell immersed in a gene-dispersed culture medium; and pushing down the flexible support part toward the substrate, further from a position where a tip of the fine needle contacts the substrate.

According to a third aspect of the present invention, there is provided a substance injection apparatus for injecting a substance into a cell held on a substrate, comprising:

a needle unit having a fine needle to be inserted into the cell immersed in a culture medium in which the gene is dispersed, and a flexible support part configured to hold the fine needle, the flexible support part being flexing when the fine needle is pressed onto the substrate; and a drive unit configured to push down the flexible support part toward the substrate, further from a position where a tip of the fine needle contacts the substrate.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 8 is a diagram explaining still another method of detecting the contact between the needle and a surface of a substrate.

FIG. 9A is a laser scanning microscope image of a HelaS3 cells immersed in a fluorescent dye solution.

FIG. 9B is a photomicrograph showing the cells into which a dye solution has been injected by using the gene injection method according to the first embodiment of the invention.

FIG. 10A is a photomicrograph of HelaS3 cells, taken immediately after injecting genes encoding GFP fluorescent protein, into the cells by using the gene injection apparatus and gene injection method according to the first embodiment.

FIG. 10B is a photomicrograph of the HelaS3 cells, taken with a phase-contrast microscope, 24 hours after injecting genes encoding GFP fluorescent protein, into the cells by using the gene injection apparatus and gene injection method according to the first embodiment.

FIG. 10C is a photomicrograph of the HelaS3 cells, taken with a fluorescent microscope, 24 hours after injecting genes encoding GFP fluorescent protein, into the cells by using the gene injection apparatus and gene injection method according to the first embodiment.

DETAILED DESCRIPTION OF THE INVENTION

The best mode of practicing the present invention will be described, with reference to the accompanying drawings.

First Embodiment

A gene injection apparatus and a gene injection method, both according to a first embodiment of the invention, will be described with reference to FIG. 1 to FIG. 8.

Figure 1:
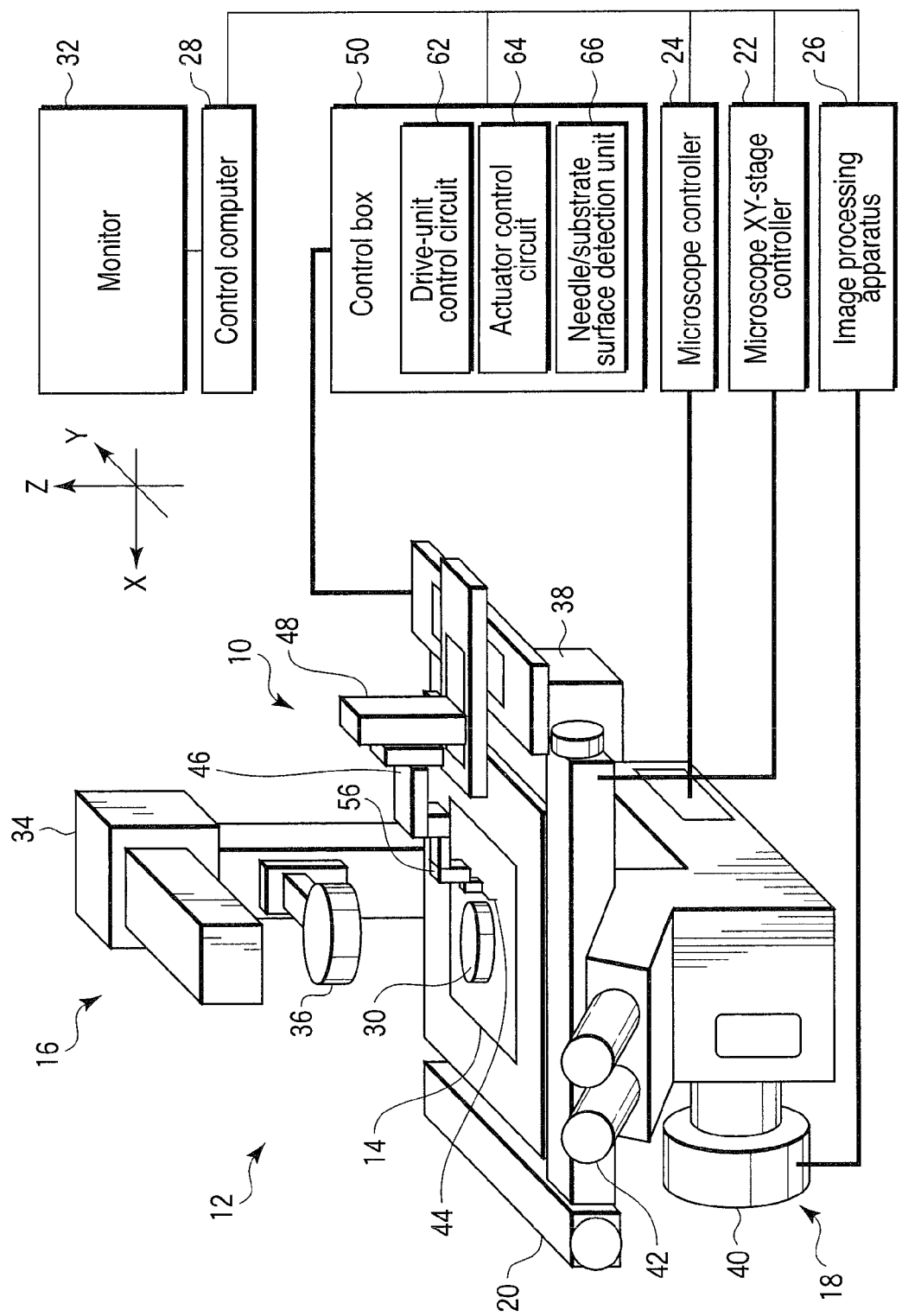
FIG. 1 is a diagram showing the overall configuration of a gene injection apparatus according to a first embodiment of this invention.

A gene injection apparatus 10 according to this embodiment is designed for use in combination with an inverted microscope 12 through which cells may be observed, as shown in FIG. 1. The inverted microscope 12 includes a work holder 14, an illumination device 16, an observation device 18, a microscope XY stage 20, a microscope XY-stage controller 22, a microscope controller 24, an image processing apparatus 26, and a control computer 28.

The work holder 14 holds a work 30 that contains cells. The illumination device 16 applies light to the cells mounted on the work holder 14. The observation device 18 detects light reflected from, or passing through, the cells, or the fluorescent light from the cells. The microscope XY stage 20 is configured to move the work holder 14 in X and Y directions, as it is driven by the microscope XY-stage controller 22.

The microscope controller 24 controls the illumination device 16 and the observation device 18. The image processing apparatus 26 processes the image which the observation device 18 has acquired. The control computer 28 controls the gene injection apparatus 10 and the inverted microscope 12 and has a monitor 32 that displays the image the image processing apparatus 26 has processed.

The work 30 has a substrate that is made of transparent material, such as glass, so that the cells it holds may be observed.

The illumination device 16 includes an illumination light source 34, a condenser lens 36, and an epi-illumination light source 38. The illumination light source 34 is located above the observation device 18 and configured to apply illumination light to the cells from above the work 30. The condenser lens 36 focuses the illumination light emitted from the illumination light source 34, at the cells located above the observation device 18. The epi-illumination light source 38 is configured to apply illumination light to the cell from below the cells, i.e., from the side where the observation device 18 is located.

The observation device 18 includes an observation optical system including an objective lens (not shown), a CCD camera 40 which receives light coming from the cells through the observation optical system and acquires an image of the cells, and an eyepiece 42 through which the user can directly observe the cells.

The gene injection apparatus 10 according to this embodiment is arranged near the work holder 14 of the inverted microscope 12 and includes a needle 44, a needle holder 46, a drive unit 48, and a control box 50. The needle 44 is a fine needle that may be inserted into the cell and is held by the needle holder 46. The drive unit 48 moves the needle holder 46, which in turn moves the needle 44. The drive unit 48 has a three-axis linear translation mechanism that can move the needle 44 in X, Y and Z directions. The control box 50 controls the components of the gene injection apparatus 10.

Figure 2:
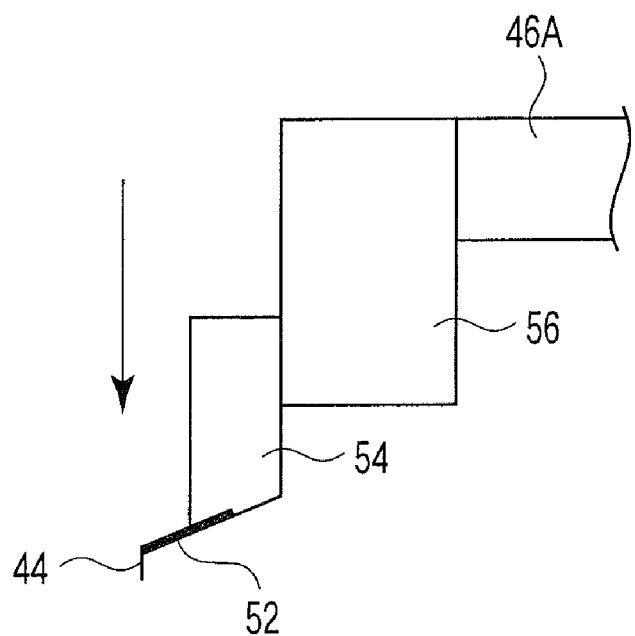
FIG. 2 is a magnified view showing the structure of a cantilever and some components near the cantilever.

As shown in FIG. 2, the needle 44 is held at the free end of a cantilever 52, extending at an intersectional direction to the lengthwise direction of the cantilever 52. The cantilever 52 is fastened to a holding member 54, which in turn is fixed to the arm 46A of the needle holder 46 via a Z-axis actuator 56. The cantilever 52 is thus held, extending slantwise and downward, and the needle 44 is held at the free end of the cantilever 52, extending downward in the vertical direction as the arrow indicates in FIG. 2.

Figure 3:
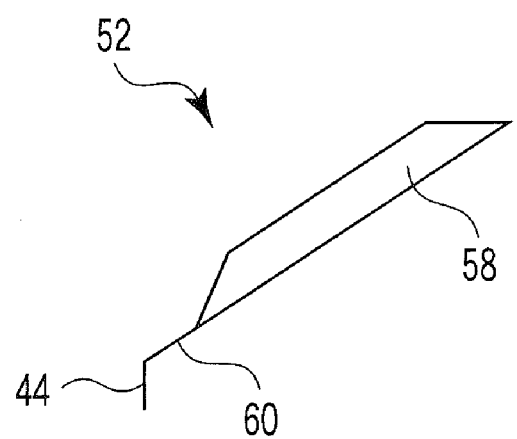
FIG. 3 is a magnified view illustrating the structure of the cantilever.

As shown in FIG. 3, the cantilever 52 is composed of a flexible silicon base 58 and a lever part 60 which holds, at the distal end, the needle 44 that is minute slender. The cantilever 52 can be detached from the holding member 54 and replaced by a new one. Hence, if the cantilever 52 is replaced with a new cantilever, the gene injection apparatus 10 can be repeatedly used without any possibility of contamination.

The Z-axis actuator 56 arranged between the holding member 54 and the needle holder 46 is, for example, stacked piezoelectric elements. The actuator 46 therefore elongates or contracts in accordance with the voltage applied to it. As FIG. 2 shows, the Z-axis actuator 56 extends in the vertical direction between the holding member 54 and the needle holder 46. The actuator 56 can therefore move the holding member 54 in the vertical direction by a very short distance, to and from the needle holder 46 by controlling the applied voltage. Hence, the needle 44, which is attached to the holding member 54 and extends downward from the holding member 54, can move the injection in the vertical direction by a very short distance.

The control box 50 includes a drive-unit control circuit 62, an actuator control circuit 64, and a needle/substrate surface detection unit 66. The drive-unit control circuit 62 controls the drive unit 48, and the actuator control circuit 64 controls the Z-axis actuator 56. The needle/substrate surface detection unit 66 detects whether the tip of the needle 44 has contacted the substrate surface of the work 30.

A gene injection method using the gene injection apparatus 10 configured as described above will be explained.

When a gene is injected into a cell being cultured in the culture solution medium contained in the work 30, by using the gene injection apparatus 10 according to the present embodiment, a gene-injecting substance is first dispersed in the culture medium. Then, the microscope XY-stage controller 22 and the microscope controller 24 are driven, moving the microscope XY stage 20, thereby being placed the cell to be observe in the view field of the inverted microscope 12. Thereafter, the drive-unit control circuit 62 controls the drive unit 48, which moves the cantilever 52 downward, ultimately moving the needle 44 toward the cell from above. The downward motion of the needle 44 from a position near the cell is achieved as the actuator control circuit 64 controls the Z-axis actuator 56, because the thickness of the cell placed on the substrate of the work 30 is only about 2 to 10 μm.

Figure 4A:
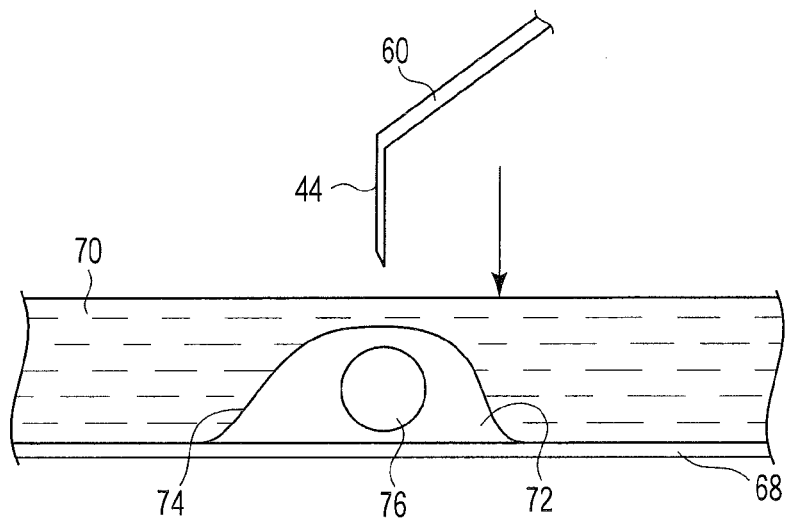
FIG. 4A is a diagram showing the first state the needle provided on the cantilever explaining a gene injection method according to the first embodiment of the invention.

As the Z-axis actuator 56 is driven, the needle 44 moves down, approaching the substrate 68 of the work 30 as is illustrated in FIG. 4A. As the needle 44 moves down, its tip enters the culture medium (hereinafter called "DNA-dispersed solution 70") in which the genes are dispersed, and eventually contacts the cell 72 held on the substrate 68. The needle 44 is further lowered until it pierces the cell membrane 74, entering the nucleus 76.

Figure 4B:
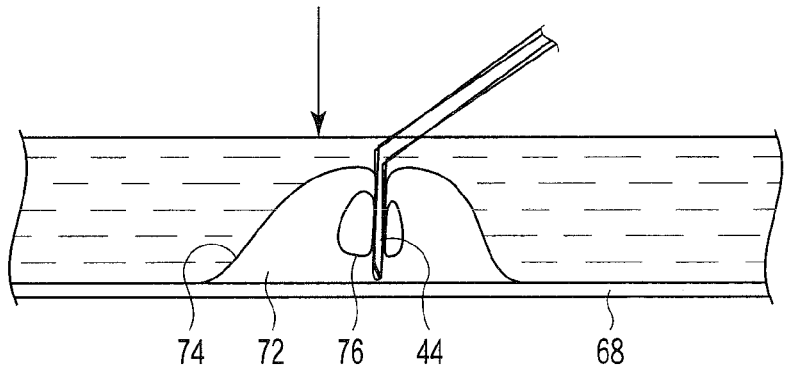
FIG. 4B is a diagram showing the second state the needle provided on the cantilever explaining a gene injection method according to the first embodiment of the invention.
Figure 4C:
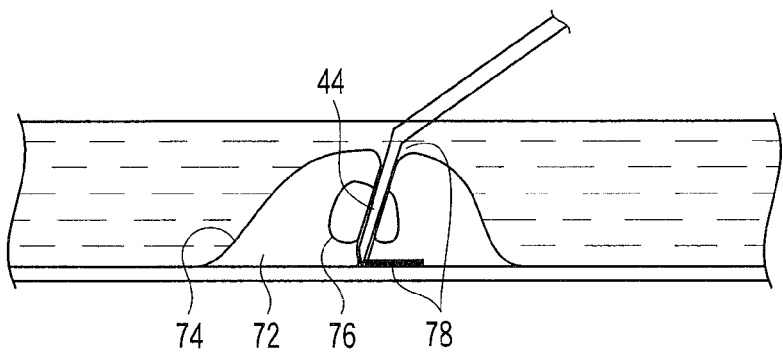
FIG. 4C is a diagram showing the third state the needle provided on the cantilever explaining a gene injection method according to the first embodiment of the invention.
Figure 5:
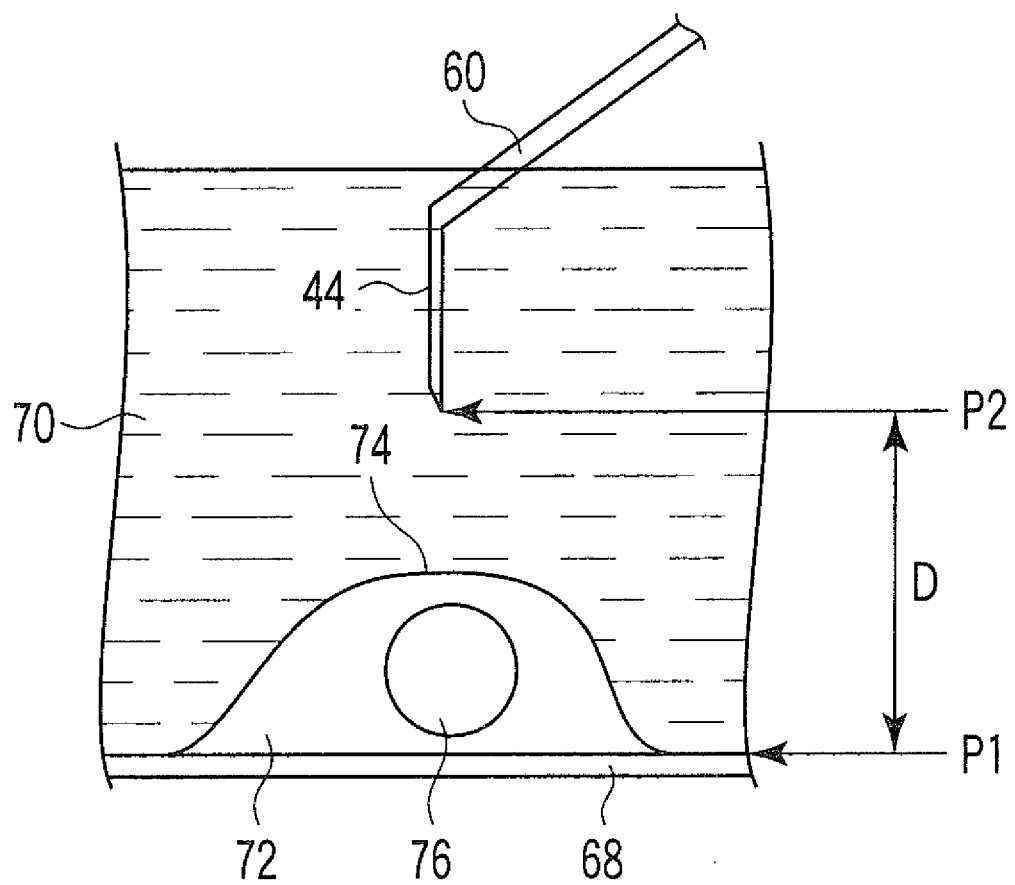
FIG. 5 is a diagram explaining a method of detecting the contact between the needle and a surface of a substrate.

Next, when the needle/substrate surface detection unit 66 detects that the needle 44 has been lowered to the position where its tip contacts the substrate surface 68 as shown in FIG. 4B, the needle 44 is further moved downward from the position. As a result, as shown in FIG. 4C, the tip of the needle 44 slides on the substrate surface 68, tearing the cell membrane 74 and puncturing the cell membrane 74 at a tearing position 78. The bottom part of the cell membrane 74 is torn, too. Thus, a through hole which pierces between the tearing position 78 in the upper part of the cell membrane 74 and the tearing position 78 in the lower part thereof is made.

Through the through hole thus made in the cell membrane 74, the DNA-dispersed solution 70 flows into the cell 72, whereby the gene in the solution enters the cell 72.

The needle 44 is then moved up and withdrawn from the cell 72. A prescribed time thereafter having elapsed, the cell membrane 74 is self-restored. The gene is therefore entrapped in the cell 72.

Thus, the present embodiment can inject the gene into the cell 72 at high reliability and efficiency, while maintaining the cell at as high a survival rate as the conventional apparatus does.

As described above, the needle 44 slides on the substrate surface 68 as it is lower even after it has contacted the substrate surface 68. The method of sliding the needle 44 on the substrate surface 68 is not limited to this, nevertheless. For example, the arm 46A of the needle holder 46 may be composed of stacked piezoelectric elements, like the Z-axis actuator 56. In this case, the arm 48A can elongate and contract to slide the needle 44 in the horizontal direction, with its tip set in contact with the substrate 68.

Of course, the Z-axis actuator 56 and the arm 46A need not be composed of piezoelectric elements if the drive unit 48 can so minutely move the needle 44 in the X, Y and Z directions.

To detect the contact between the needle 44 and the substrate surface 68, the needle/substrate surface detection unit 66 first measures the focus position of the substrate surface 68 and that of the tip of the needle 44 and then calculates the relative distance between the substrate surface 68 and the tip of the needle 44. More precisely, the focus position P1 of the substrate surface 68 is determined by focusing the substrate surface 68 by confocal microscopy or dark-field illumination microscopy, and the focus position P2 of the tip of the needle 44 is determined by focusing the tip of the needle 44 by confocal microscopy or dark-field illumination microscopy. Then, the following operation is performed, finding the distance between the substrate surface 68 and the tip of the needle 44:

(P2−P1)×refractive index of DNA-dispersed solution 70

It is when the relative distance thus found is zero that the tip of the needle 44 contacts the substrate surface 68. Hence, the needle 44 may be gradually lowered, while continuously measuring the relative distance. Alternatively, the relative distance may be measured only once. In this case, the needle 44 only needs to be lowered further by the relative distance measured until it contacts the substrate surface 68.

Figure 6A:
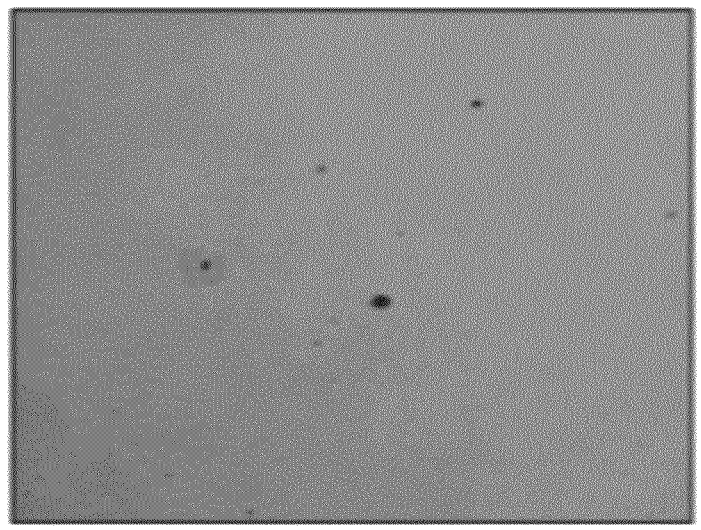
FIG. 6A is a photomicrograph focused at the surface of the substrate.
Figure 6B:
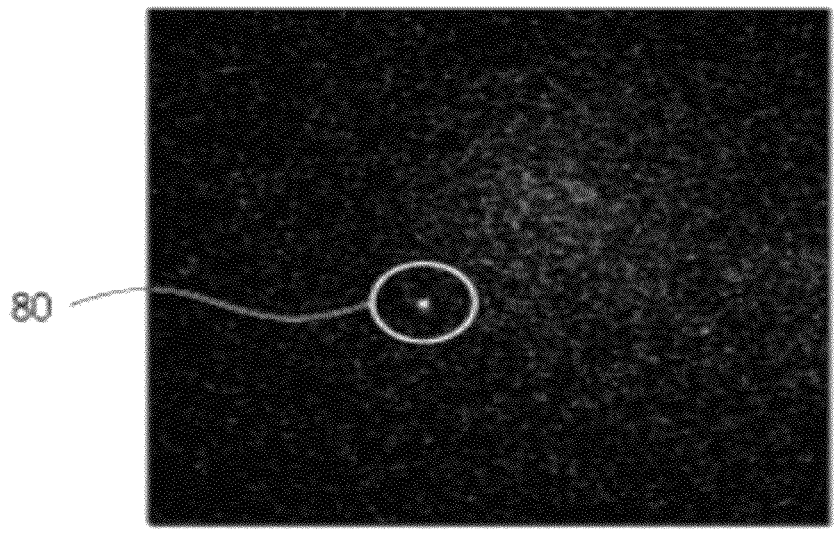
FIG. 6B is a photomicrograph focused at the tip of the needle.

FIG. 6A is a photomicrograph taken by confocal microscopy when the focal point is set at the substrate surface 68. When the focal point is set at the substrate surface 68, the position of the objective lens assumes the focus position P1. FIG. 6B is a photomicrograph taken by confocal microscopy when the focal point is set at the tip of the needle 44. When the focal point is set at the tip of the needle 44, the position of the objective lens assumes the focus position P2. In FIG. 6B, the white dot at the center of circle 80 indicates the tip of the needle 44.

Figure 7:
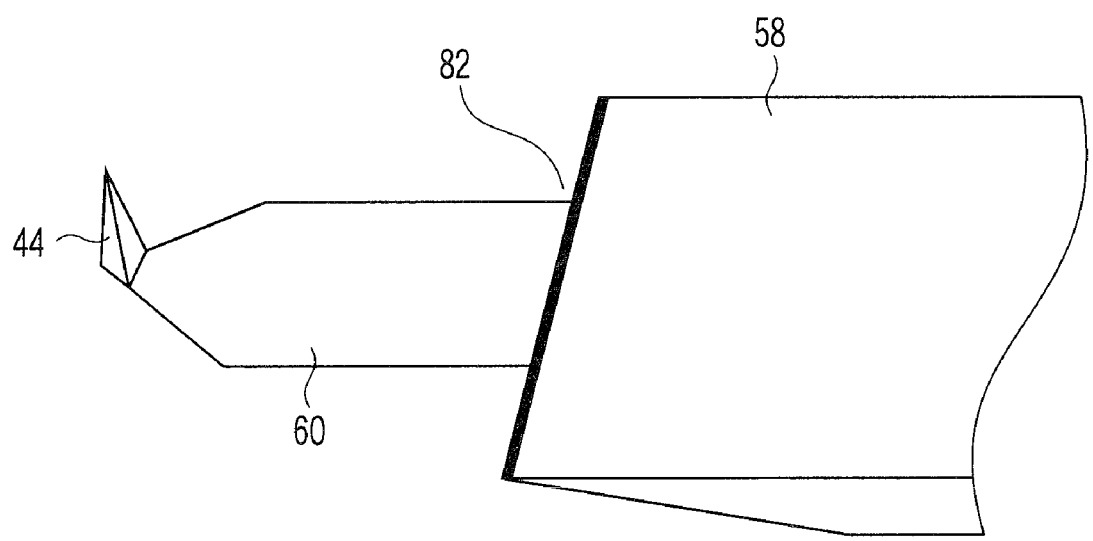
FIG. 7 is a diagram explaining another method of detecting the contact between the needle and a surface of a substrate.

The focal point may be determined by focusing at a point other than the tip of the needle 44. The focal point is set at, for example, the boundary 82 between the silicon base 58 and the lever part 60 as shown in FIG. 7, because the sizes of the silicon base 58 and lever part 60 are known.

The needle/substrate surface detection unit 66 may detect the contact between the needle 44 and the substrate surface 68 in a different way. For example, the unit 66 may detect the contact from a change in the position where the tip of the needle 44 exists on the substrate surface 68, which takes place as the silicon base 58 flexes and which is detected in the microscope image shown in FIG. 8. In this case, the needle 44 is pulled up by a prescribed sliding distance in accordance with the positional change the needle 44 undergoes on the substrate surface 68. In FIG. 8, number 84 shows the position of the tip of the needle 44 at penetration depth of 0 μm, and number 86 shows the position of the tip of the needle 44 at penetration depth of 10 μm.

The distance may be measures for each cell, or for only one point in the observation area. In the latter case, the measured distance is applied to all cells existing in the observation area.

Example 1

FIG. 9A is a photomicrograph of HelaS3 cells, taken with a laser scanning microscope, while the cells ware being immersed in a fluorescent dye solution. The photomicrograph shows a section of the cells, taken along a horizontal plane 2 to 3 μm above the substrate surface on which the cells are held. The fluorescent dye contained in the solution is sulforhodamine. Since the fluorescent of the dye is detected by using the laser scanning microscope, in this figure, a part of the solution which surrounds the cells is observed.

In Embodiment 1, the needle 44 is lowered after entering the cell, deeper from the position where its tip contacts the substrate surface 68. The tip part of the needle 44 therefore slides for about 3 μm on the substrate surface 68 and pierces the cell to inject the dye solution into the cell. FIG. 9B shows the result of the injection. Since the dye solution has flowed into the cell 72A made the through hole from the region around the cell 72A, the fluorescence in the cell 72A will increase, which indicates that fluorescent has been injected into the cell 72A.

Example 2

As in Example 1, HelaS3 cells are immersed in a gene-dispersed solution in order to inject the gene into the HelaS3 cells. The injected gene encodes GFP fluorescent protein. Whether the gene has been injected into the cell can be determined in accordance with whether fluorescent light is observed in the cell.

FIG. 10A is a microscope image of cells, photographed immediately after genes have been injected into cells. The genes have been injected into a plurality of cells in FIG. 10A. FIGS. 10B and 10C are images of cells, taken 24 hours after injecting the gene into each cell, from which to determine whether a gene has been successfully injected. More precisely, FIG. 10B is a phase-contrast image showing the state the cells 24 hours after the injection of genes. FIG. 10C is an image of the cells observed by fluorescent microscopy, indicating that the cells introduced the genes express the genes and emit intense fluorescent light. The intense fluorescent light reveals that the genes have been injected into the cells with very high efficiency.

Second Embodiment

A gene injection apparatus and a gene injection method, both according to a second embodiment of this invention, will be described with reference to FIGS. 11 and 12.

Figure 11:
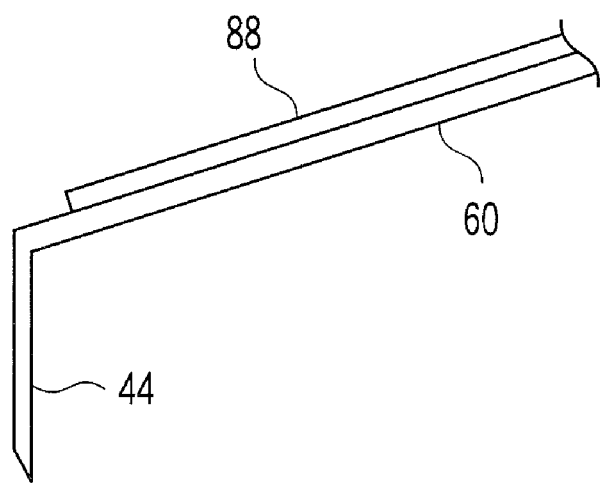
FIG. 11 is a magnified view showing the structure of the cantilever incorporated in a gene injection apparatus according to a second embodiment of this invention.

As shown in FIG. 11, a sensor 88 is attached to the lever part 60 of the cantilever 52 and is used to detect how much the lever part 60 has flexed. Using the sensor 88, the needle/substrate surface detection unit 66 detects whether the tip of the needle 44 has contacted the substrate surface 68. The sensor 88 is, for example, a PZT whose resistance varies with the degree of flexing.

The lever part 60 has such hardness that it does not flex when the needle 44 abuts the surface of the cell membrane 74 and that its end does not be broken even if it flexes by height of about 10 μm.

The gene injection method performed by using the gene injection apparatus 10 according to this embodiment will be explained below.

When a gene is injected into a cell being cultured in the culture medium contained in a work 30, by using the gene injection apparatus 10 according to this embodiment, a gene-injecting substance is first dispersed in the culture medium. Then, the microscope XY-stage controller 22 and the microscope controller 24 are driven, moving the microscope XY stage 20, thereby being placed the cell to be observed in the view field of the inverted microscope 12. Thereafter, the drive-unit control circuit 62 controls the drive unit 48, which moves the cantilever 52 downward, ultimately moving the needle 44 toward the cell from above. The downward motion of the needle 44 from a position near the cell is achieved as the actuator control circuit 64 controls the Z-axis actuator 56, because the thickness of the cell placed on the substrate of the work 30 is only about 2 to 10 μm.

As the Z-axis actuator 56 is driven, the needle 44 moves down, approaching the substrate 68 of the work 30. As the needle 44 moves down, its tip enters the DNA-dispersed solution 70 contained in the work 30, and eventually contacts the cell 72 held on the substrate 68 of the work 30. The needle 44 is further lowered until it enters the cell 72, i.e., the cell membrane 74 and the nucleus 76. When the needle 44 abuts the cell 72, it does not flex at all because of the hardness of the lever part 60. Thus, the needle 44 is lowered to the substrate surface 68.

Figure 12:
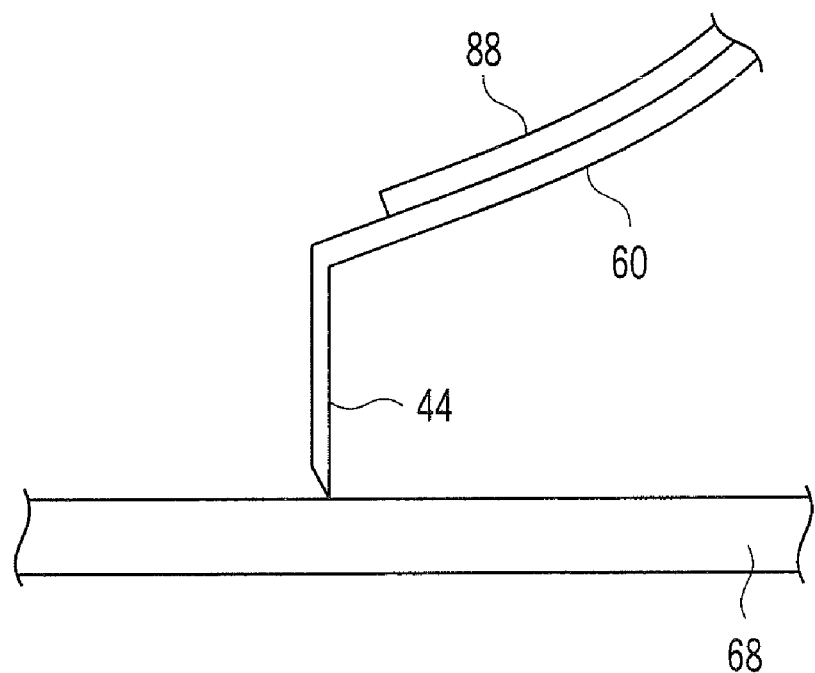
FIG. 12 is a diagram illustrating an arm section that is bent as a needle contacts the surface of the substrate.

When the needle 44 contacts the substrate surface 68, the lever part 60 flexes as is illustrated in FIG. 12, changing the resistance of the sensor 88. The needle/substrate surface detection unit 66 detects the change in the resistance of the sensor 88, which is equivalent to the degree of flexing of the lever part 60. From the degree of flexing, the detection unit 66 can determine that the needle 44 has been lowered to contact the substrate surface 68. The needle 44 is further lowered from the potion where it contacts the substrate surface 68 until the lever part 60 further flexes by a preset distance, for example, by a few microns. In other words, the Z-axis actuator 56 is driven until the sensor 88 detects that the lever part 60 has flexed by a preset amount. When the lever part 60 flexes by the preset amount, the Z-axis actuator 56 is driven in the direction it contracts, thereby pulling up the needle 44. As a result, the needle 44 slides on the substrate surface 68, breaking the tearing portion 78 of the cell membrane 74, thereby making a through hole in the cell membrane 74.

Through the through hole thus made in the cell membrane 74, the DNA-dispersed solution 70 flows into the cell 72, whereby the gene in the DNA-dispersed solution 70 enters the cell 72.

The needle 44 is then moved up and withdrawn from the cell 72. A prescribed time thereafter having elapsed, the cell membrane 74 is self-restored. The gene is therefore entrapped in the cell 72.

Thus, in the second embodiment, the contact of the needle 44 with the substrate surface 68 can be quickly detected at high accuracy, regardless of the inclination or position change of the substrate surface 68. The apparatus 10 according to the second embodiment can therefore reliably break the cell membrane 74, while being least invasive to the cell 72.

The present invention has been described with reference to the embodiments described above. The invention is not limited to the embodiments, nevertheless. Various changes and modifications can of course be made within the scope and spirit of the invention.

For example, the substance to be injected into the cell is not limited to a gene. Other substances that can be dispersed in solutions, such as dyes, fluorescent reagents (e.g., quantum dots), ions, peptides, proteins, polysaccharides, may be injected into the cell.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A gene injection apparatus for injecting a gene into a cell held on a surface of a substrate, comprising:
    a fine needle to be inserted into the cell immersed in a culture medium in which the gene is dispersed; and
    a drive unit configured to slide a tip of the fine needle along the surface of the substrate.

2. The gene injection apparatus according to claim 1, wherein:
    the fine needle further comprises a flexible support part configured to hold the fine needle, the flexible support part being flexing when the fine needle is pressed onto the substrate, thereby sliding a tip of the fine needle along the substrate and preventing the tip of the fine needle from being broken; and
    the drive unit is configured to push down the flexible support part toward the substrate, further from a position where a tip of the fine needle contacts the substrate.

3. The gene injection apparatus according to claim 2, wherein the flexible support part has such hardness that the fine needle remains unchanged in state while pressed onto the cell, and flexes when pressed onto the substrate, the hardness is set to not allow the fine needle to flex on a surface of a cell membrane and not to break after the flexible support flexes about 10 μm.

4. The gene injection apparatus according to claim 2, further comprising a detecting unit configured to detect an amount of flexing of the flexible support part, wherein the drive unit pushes down the flexible support part to a position where the flexible support part flexes by a preset amount, in accordance with the amount of flexing the detecting unit has detected.

5. The gene injection apparatus according to claim 2, wherein the flexible support part comprises a leaf spring-like lever portion in which one end is a free end and the other end is held slantwise with respect to the substrate surface.

6. The gene injection apparatus according to claim 5, further comprising:
    a detector configured to detect a sliding distance of the fine needle by the drive unit, the detector comprising:
        a camera configured to observe one of the fine needle and the free end of the lever portion; and
        a determination portion configured to determine the sliding distance from a positional change of one of the fine needle and the free end of the lever portion.

7. A gene injection method for injecting a gene into a cell held on a substrate, by using a fine needle to be inserted into the cell immersed in a culture medium in which the gene is dispersed, the method comprising:
- inserting the fine needle into the cell immersed in a gene-dispersed culture medium; and
- sliding a tip of the fine needle along the surface of the substrate.

8. The gene injection method according to claim 7, wherein the fine needle and a flexible support part configured to hold the fine needle, the flexible support part being flexed when the fine needle is pressed onto the substrate, the method further comprises:
- inserting the fine needle into the cell immersed in a gene-dispersed culture medium; and
- pushing down the flexible support part toward a surface of the substrate, further from a position where a tip of the fine needle contacts the substrate, thereby sliding a tip of the fine needle along the substrate and preventing the tip of the fine needle from being broken, wherein the fine needle slides on the surface of the substrate.

* * * * *